(12) United States Patent
Van Mourik et al.

(10) Patent No.: US 9,221,775 B2
(45) Date of Patent: Dec. 29, 2015

(54) ALKYLENE OXIDE PRODUCTION

(71) Applicant: SHELL OIL COMPANY, Houston, TX (US)

(72) Inventors: Arian Van Mourik, Amsterdam (NL); Ingmar Hubertus Josephina Ploemen, Amsterdam (NL)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 14/580,683

(22) Filed: Dec. 23, 2014

(65) Prior Publication Data

US 2015/0191440 A1    Jul. 9, 2015

(30) Foreign Application Priority Data

Jan. 3, 2014  (EP) .................................... 14150139

(51) Int. Cl.
| | |
|---|---|
| *C07D 301/03* | (2006.01) |
| *C07D 301/19* | (2006.01) |
| *C07D 301/04* | (2006.01) |
| *C07C 407/00* | (2006.01) |
| *B01D 17/04* | (2006.01) |
| *C07C 7/11* | (2006.01) |

(52) U.S. Cl.
CPC ............ *C07D 301/04* (2013.01); *B01D 17/045* (2013.01); *C07C 7/11* (2013.01); *C07C 407/00* (2013.01)

(58) Field of Classification Search
CPC .. C07D 301/19; C07D 303/04; C07D 301/04; C07D 407/00; C07D 409/08; C07D 7/11; C07D 15/073; B01D 17/045
USPC ................................................. 549/529, 523
See application file for complete search history.

(56) References Cited

U.S. PATENT DOCUMENTS

| | | |
|---|---|---|
| 5,512,175 A | 4/1996 | Saito et al. |
| 5,883,268 A | 3/1999 | Lin et al. |

FOREIGN PATENT DOCUMENTS

| | | |
|---|---|---|
| EP | 345856 | 12/1989 |
| WO | 9942425 | 8/1999 |
| WO | 9942426 | 8/1999 |
| WO | 2004076408 | 9/2004 |
| WO | 2005005402 | 1/2005 |
| WO | 2005016903 | 2/2005 |
| WO | 2007116046 | 10/2007 |
| WO | 2007126666 | 11/2007 |

OTHER PUBLICATIONS

Liquid Coalescer Design Manual of ACS Industries, LP, Houston, Texas, USA.

*Primary Examiner* — T. Victor Oh

(57) ABSTRACT

A process for preparing an alkylene oxide comprising contacting an alkyl phenyl hydroperoxide with an alkene in an epoxidation reaction to obtain an alkylene oxide and an alkyl phenyl alcohol, wherein the alkyl phenyl hydroperoxide is prepared by a process comprising reacting an alkyl aryl compound and oxygen to produce a reaction mixture comprising alkyl phenyl hydroperoxide, alkyl aryl compound and oxygen; separating at least a part of the reaction mixture into a product stream comprising alkyl phenyl hydroperoxide and an alkyl aryl compound stream; mixing at least a part of the alkyl aryl compound stream with a basic aqueous solution; separating at least a part of the mixture of alkyl aryl compound and basic aqueous solution with the help of a coalescer to obtain an organic phase containing alkyl aryl compound, and an aqueous phase; and recycling at least a part of the organic phase to the reacting step.

10 Claims, 2 Drawing Sheets

ALKYLENE OXIDE PRODUCTION

This non-provisional application claims the benefit of European Application No. 14150139.5 filed Jan. 3, 2014, which is hereby incorporated by reference in its entirety.

FIELD OF THE INVENTION

The present invention relates to a process for preparing an alkylene oxide.

BACKGROUND OF THE INVENTION

As described in EP345856, alkylene oxides may be prepared by contacting an alkyl phenyl hydroperoxide with an alkene to obtain an alkylene oxide and an alkyl phenyl alcohol. The alkyl phenyl alcohol may then be converted by dehydration into the corresponding aromatic alkene.

The afore-mentioned epoxidation and dehydration processes are typically employed in the co-production of propylene oxide and styrene from ethyl benzene hydroperoxide and propylene.

Alkyl phenyl hydroperoxides used in such epoxidation reactions may be prepared by reacting an alkyl aryl compound and oxygen to produce a reaction mixture comprising alkyl phenyl hydroperoxide, alkyl aryl compound and oxygen. The reaction mixture may be separated into a liquid phase comprising alkyl phenyl hydroperoxide, and a vapour phase comprising alkyl aryl compound and oxygen. The liquid phase comprising the desired alkyl phenyl hydroperoxide product may then be used in the preparation of the alkylene oxide. The vapour phase comprising alkyl aryl compound and oxygen may be condensed, and the condensate at least partly recycled to prepare further alkyl phenyl hydroperoxide.

If the oxidation of the alkyl aryl compound proceeds with low selectivity, then the reaction may also produce by-products such alkyl phenyl alcohol and alkyl phenyl ketone.

Besides the desired alkyl phenyl hydroperoxide and the afore-mentioned by-products, a wide range of additional contaminants are created during the oxidation of alkyl aryl compounds. Although most of these contaminants are present in small amounts, the presence of the organic acids especially has been found to cause problems in the further use of the alkyl phenyl hydroperoxide in epoxidation. It is therefore known to contact the liquid phase of the reaction mixture with aqueous base in an amount sufficient to neutralize acidic components, e.g. as described in WO2004076408. Subsequently the resulting mixture can be phase-separated into separate aqueous and organic (hydrocarbonaceous) phases. The organic phase, which contains some base, can then be water washed to further separate the basic materials, e.g. as described in WO2007116046.

In circumstances wherein it is desirable to co-produce alkylene oxides and aromatic alkenes, then it is possible to convert alkyl phenyl alcohol and alkyl phenyl ketone by-products resulting from the oxidation of alkyl aryl compounds into their corresponding aromatic alkenes, thereby increasing the overall yield of aromatic alkene from the integrated process to produce alkylene oxide and aromatic alkene.

However, there are times when market conditions do not favour the co-production of aromatic alkenes along with alkylene oxide. Under such circumstances it is desirable to minimise the amount of alkyl phenyl alcohol and alkyl phenyl ketone co-produced during the oxidation of alkyl aryl compound. That is to say, by improving the selectivity of the alkyl aryl compound oxidation to the corresponding alkyl phenyl hydroperoxide, it becomes possible to produce more alkylene oxide for every molecule of co-produced aromatic alkene.

Furthermore, it is desirable to improve the selectivity of alkyl aryl compound oxidation to the corresponding alkyl phenyl hydroperoxide in order to reduce the formation of certain undesirable contaminants that also reduce the overall feedstock yield. That is to say, by improving the selectivity of the alkyl aryl compound oxidation to the corresponding alkyl phenyl hydroperoxide, it becomes possible to lower the overall consumption of alkyl aryl compound for every molecule of alkylene oxide produced.

For example, with regard to the co-production of propylene oxide and styrene from ethyl benzene hydroperoxide, formation of 1-phenylethanol and acetophenone during the oxidation of ethylbenzene will increase the overall production of styrene vis-à-vis propylene oxide in an integrated process. However, in times when market demand for styrene is low, it is preferable to minimise formation of such by-products in order to be able to increase the production of propylene oxide for every molecule of co-produced styrene.

In the preparation of ethyl benzene hydroperoxide according to the above general process on an industrial scale, a drop in selectivity has been observed over a prolonged time, as a creeping trend. However, for the reasons described above, a high selectivity of the oxidation reaction is of importance in an industrial context in the manufacture of alkylene oxide. Thus, even small losses in selectivity during the afore-mentioned oxidation reaction can have a major impact on the economy of production of alkylene oxide therefrom. Moreover, the smaller amounts of by-products that cannot be converted into either propylene oxide or styrene which are formed during the oxidation step need to be minimized at any time in order to maximize the overall economics of the process.

It is an object of the invention to address selectivity drops during the preparation of alkyl phenyl hydroperoxide from alkyl aryl compound and oxygen, thereby improving the overall selectivity of a process for preparing an alkylene oxide by preparing producing more alkylene oxide for every molecule of co-produced aromatic alkene and minimizing the amount of waste.

SUMMARY OF THE INVENTION

Figure 1:
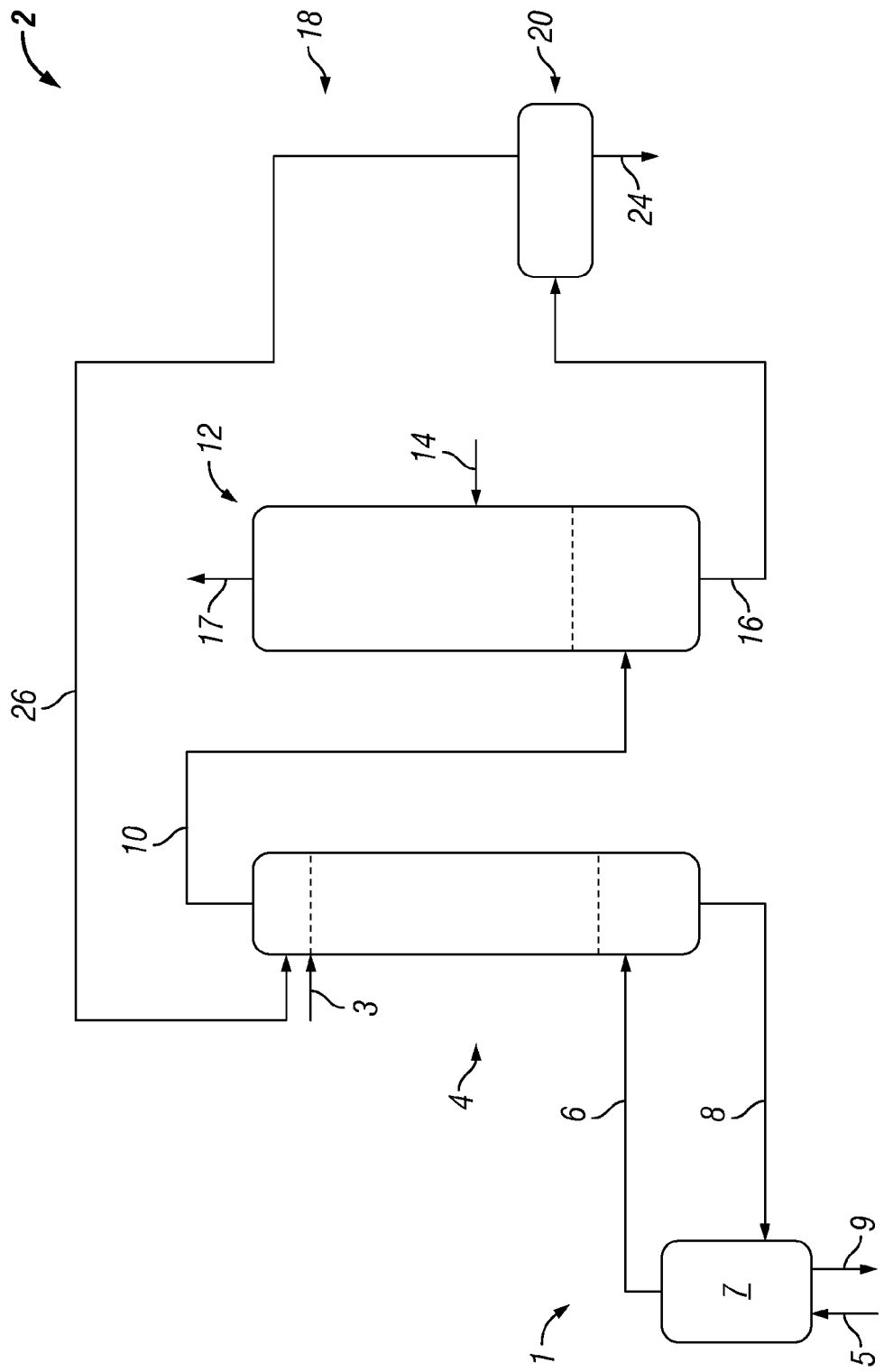
FIG. 1 depicts an embodiment of the invention.

Following an extensive investigation, it has now been found that a selectivity drop in the preparation of alkyl phenyl hydroperoxide may occur as a result of alkali metal content in a recycled stream comprising alkyl aryl compound.

In particular, a selectivity drop observed in the preparation of ethyl benzene hydroperoxide was found to be linked to oxygen supply in an oxidation reactor, caused by fouling. The fouling was in turn found to be caused by alkali metal in a recycled ethylbenzene stream. The alkali metal in the recycled ethylbenzene stream originated from the neutralisation of said stream with a basic aqueous solution, which was performed to reduce acid contaminants.

Aspects of the invention reside in the recognition and advantageous resolution of this problem, leading to surprising benefits in the overall selectivity in the manufacture of alkylene oxide for every molecule of co-produced aromatic alkene.

From one aspect, the invention provides a process for preparing an alkylene oxide comprising preparing an alkyl phenyl hydroperoxide and contacting the alkyl phenyl hydroperoxide with an alkene in an epoxidation reaction to obtain an alkylene oxide and an alkyl phenyl alcohol, wherein the alkyl phenyl hydroperoxide is prepared by a process comprising:

(a) reacting an alkyl aryl compound and oxygen to produce a reaction mixture comprising alkyl phenyl hydroperoxide, alkyl aryl compound and oxygen;

(b) separating at least a part of the reaction mixture into a product stream comprising alkyl phenyl hydroperoxide and a stream comprising alkyl aryl compound;

(c) mixing at least a part of the separated alkyl aryl compound stream with a basic aqueous solution;

(d) separating at least a part of the mixture of step (c) with the help of a coalescer to obtain a separated organic phase containing alkyl aryl compound, and a separated aqueous phase; and (e) recycling at least a part of the separated organic phase containing alkyl aryl compound to step (a).

Separation of the mixture of step (c) with a coalescer has been found to mitigate fouling during step (a), which has in turn been found to help maintain selectivity of the process towards the alkyl phenyl hydroperoxide product.

DETAILED DESCRIPTION

The alkyl aryl compound used in the present invention may in principle be any alkyl aryl compound capable of being oxidised to form an alkyl aryl hydroperoxide. Advantageously, the alkyl aryl compound may comprise or consist of carbon and hydrogen. Alkyl aryl compounds which are most frequently used are benzene compounds containing at least 1 alkyl substituent which alkyl substituent contains in the range of from 1 to 10 carbon atoms, preferably in the range of from 2 to 8 carbon atoms. Preferably, the benzene compound contains on average from 1 to 2 substituents. More preferred alkyl aryl compounds are ethylbenzene, cumene, sec-butylbenzene and di(iso-propyl)benzene. Most preferably the alkyl aryl compound is ethylbenzene. When ethylbenzene is used as the alkyl aryl compound, the process can be used to prepare ethylbenzene hydroperoxide. That is to say, in a preferred embodiment of the present invention, the alkyl aryl compound is ethylbenzene and the alkyl phenyl hydroperoxide is ethyl benzene hydroperoxide.

The oxidation of the alkyl aryl compound in step (a) of the process can be carried out in any suitable manner known in the art. The reaction with oxygen may suitably be achieved by contacting the alkyl aryl compound with an oxygen-containing gas or gas mixture, such as for example air. The oxidation can be carried out in the liquid phase in the presence of a diluent. The diluent can be a compound necessarily present during the reaction. For example, if the alkyl aryl compound is ethylbenzene the diluent can be ethylbenzene as well. In an embodiment step (a) may thus involve preparing a solution of ethyl benzene hydroperoxide in ethylbenzene. Other suitable diluents may be compounds that are liquid under the reaction conditions and which do not significantly react with the starting materials and product obtained.

The reaction mixture produced in step (a) from oxidation still comprises oxygen. Typically, a vapour part of the reaction mixture comprises oxygen (typically mixed with other air gases), as well as vapour of the alkyl aryl compound.

In step (b) of the process, at least a part of the reaction mixture, and optionally the entirety thereof, is separated into a stream comprising alkyl phenyl hydroperoxide and a stream comprising alkyl aryl compound. Suitably step (b) may comprise separating at least a part of the reaction mixture into: a liquid stream comprising alkyl phenyl hydroperoxide and alkyl aryl compound; and a vapour stream comprising alkyl aryl compound and oxygen. Conveniently, step (b) may be performed within an oxidation zone, e.g. an oxidation reactor, in which step (a) is performed. For example a vapour stream comprising alkyl aryl compound and oxygen may be obtained as an offgas stream from such a zone or reactor.

Before step (c), at least part of the stream comprising alkyl aryl compound, and optionally the entirety thereof, may optionally be subjected to one or more preliminary steps, for example a heat recovery step. In an embodiment where said stream is a vapour stream (e.g. offgas), the heat recovery step may comprise contacting at least a part of said stream with a liquid feed of alkyl aryl compound used in step (a).

Besides the desired organic hydroperoxide, a wide range of contaminants are created during the oxidation of alkyl aryl compounds. These contaminants find their way both into the product stream and the separated stream comprising alkyl aryl compound. Although most contaminants are present in small amounts, the presence of organic acids especially has been found to cause problems in the further use of hydroperoxide product. Removal of such contaminants from the product stream is therefore known, for example from U.S. Pat. No. 5,883,268 and WO2007116046.

To reduce the amount of contaminants in the separated stream comprising alkyl aryl compound, the process comprises mixing at least a part of the separated alkyl aryl compound stream, and optionally the entirety thereof, with a basic aqueous solution in step (c). Where the separated alkyl aryl compound stream is in vapour form, at least a part of the vapour stream comprising alkyl aryl compound and oxygen may be condensed and contacted with the basic aqueous solution in step (c) to form a liquid mixture for separation and recycling in steps (d) and (e). Conveniently, condensable parts of the vapour stream comprising alkyl aryl compound may be condensed by contacting said stream with basic aqueous solution in step (c).

By "mixing" is understood that the stream comprising alkyl aryl compound and the basic aqueous solution are contacted with each other in such a manner that a mixture of the two is obtained. By mixing a large interfacial area can be created between the stream comprising alkyl aryl compound and the aqueous solution, which allows mass transfer. The mixing in step (c) can be carried out in any manner known to the skilled person to be suitable for such a process, including for example by means of a static mixer, a stirred tank, a trayed or packed column or by means of fibrous contacting devices.

Preferably, a basic aqueous solution containing one or more alkali metal compounds is used. Suitable alkali sources for use in the aqueous alkali metal solution include alkali metal hydroxides, alkali metal carbonates and alkali metal hydrogen carbonates. Examples of these compounds are NaOH, KOH, $Na_2CO_3$, $K_2CO_3$, $NaHCO_3$ and $KHCO_3$.

In view of their easy availability, it is preferred to use NaOH and/or $Na_2CO_3$. The amount of alkali metal present in the aqueous alkali metal solution may vary widely. Preferably concentrations of 1 to 30% w/w of alkali metal and more preferably concentrations of 10 to 25% w/w of alkali metal based on the total aqueous solution are used.

In an embodiment, step (c) comprises dispersing at least part of the stream comprising alkyl aryl compound, and optionally the entirety thereof, into the basic aqueous solution such that the mixture obtained is a dispersion of organic droplets in an aqueous phase.

In an embodiment, step (c) comprises dispersing the basic aqueous solution into at least part of the stream comprising alkyl aryl compound, and optionally the entirety thereof, such that the mixture obtained is a dispersion of droplets of basic aqueous solution in an organic phase.

The basic aqueous solution typically comprises alkali metal and thus introduces an amount of alkali metal into the stream comprising alkyl aryl compound, which may otherwise be substantially free from alkali metal. Thus, although the amount of organic acids can be decreased by the alkali metal wash, the amount of alkali metal contaminants is increased.

As aforesaid, it has been appreciated that contaminants in the stream comprising alkyl aryl compound lead to fouling on recycling to the oxidation step (a). In step (d) the process therefore comprises separating at least part of the mixture obtained in step (c), and optionally the entirety thereof, with the help of a coalescer to obtain a separated organic phase containing alkyl aryl compound, and a separated aqueous phase, before the separated organic phase containing alkyl aryl compound is recycled to step (a).

By separation "with the help of a coalescer" is meant that the process of separation comprises at least one step in which a coalescer is contacted with at least a part of the mixture, or a pre-separated part thereof. The coalescer enhances the separation efficiency and effectiveness of step (d) and has been found to address the problem of fouling of air inlets in the reactor, and ultimately the resultant problem of a drop in selectivity.

Advantageously, the mixture obtained in step (c) may be separated in step (d) such that the organic phase has an alkali metal content of less than 20 ppm wt., preferably less than 5 ppm wt., most preferably less than 3 ppm wt.

In an embodiment, the process comprises, in step (d), passing at least a part of the mixture of step (c), and optionally the entirety thereof, to a phase separation vessel in order to separate an amount of aqueous phase therefrom, e.g. by settling and phase separation, and subsequently passing a remaining (predominantly organic) part of the mixture, resulting from this separation, to the coalescer to separate a further amount of aqueous phase therefrom. Thus, the coalescer may advantageously act in synergy with a preliminary phase separation or settling vessel.

If desired, the mixture obtained from step (c) may additionally or alternatively be filtered through a filter before contact with the coalescer. Such filters generally have openings of at most 20 micrometers, preferably of at most 10 micrometers.

The coalescer may be of any suitable type. In an embodiment, the coalescer comprises fibres selected from metal (e.g. steel), polymeric fibres, silicon treated pleated paper, and combinations thereof. In an embodiment, the coalescer comprises fluoropolymer fibres.

The coalescer for use in the present invention can be any coalescer known to be suitable to someone skilled in the art.

The coalescer will often be placed within a separation vessel, i.e. a vessel in which the separation of the aqueous phase and the organic phase can be carried out. Advantageously, at least a part of the mixture obtained from step (c), or a pre-separated part thereof, may be passed through such a coalescer separation vessel.

Separation vessels in which the coalescer can be used include vertical or horizontal vessels. One separation vessel can comprise one or more coalescers. In an embodiment, one separation vessel comprises from 1 to 50, e.g. from 1 to 10 coalescers. Such coalescers can be located in such a separation vessel in any manner known to the skilled person. For example, such coalescers can be located horizontally, diagonally or vertically in the separation vessel. In one preferred embodiment the mixture, or a pre-separated part thereof, flows through the coalescer in an essentially horizontal direction through an essentially horizontal separation vessel.

The coalescer separation vessel can contain one or more coalescers, for example in the form of a coalescer mat or a coalescer cartridge. The use of cartridges can be advantageous if a larger contact area is desired. A larger contact area allows lower space velocities.

The coalescer separation vessel may comprise a boot or sump downstream of one or more coalescers to enhance phase separation and enable a controlled removal of separated aqueous phase.

Suitable coalescers are described, for example, in "Liquid-Liquid coalescer Design Manual" of ACS Industries, LP, Houston, Tex., USA. Suitable coalescers are also commercially available, for example from Facet™ or Pall™ Corporation.

The coalescer for use in the present invention can be used in the conventional way as is known to those skilled in the art. It is customary to monitor the pressure drop over a coalescer during operation. If the pressure drop has become unacceptable, the coalescer can be cleaned for example by backwashing.

The separation of organic phase and aqueous phase in step (d) is preferably carried out in a continuous manner. In an embodiment, at least a part of the mixture obtained in step (c), or a pre-separated part thereof, is fed to a coalescer at a mass flux in the range of from 5 to 50 $m^3/hr/m^2$, for example in the range of from 15 to 25 $m^3/hr/m^2$. The pressure used during the separation can vary widely. The separation is preferably carried out in the liquid phase preferably at a pressure in the range from 0.01 to 80 bar, more preferably in a range from 0.1 to 17 bar. Preferably, the separation of organic phase and aqueous phase in step (d) is carried out at a temperature in the range of from 0° C. to 150° C., more preferably at a temperature in the range from 20° C. to 100° C., and even more preferably in the range from 40° C. to 80° C.

In an additional process step (f), at least part of the stream comprising alkyl aryl hydroperoxide, and optionally the entirety thereof, may be subjected to concentration and/or purification to obtain an alkyl aryl hydroperoxide product and then contacted with an alkene in an epoxidation step to obtain alkylene oxide and an alkyl aryl alcohol.

For example, the stream may be contacted with aqueous base, washed with water, and the resulting mixture separated with the help of a coalescer to form an organic product phase comprising the alkyl aryl hydroperoxide product.

In the process of the present invention, the alkyl aryl hydroperoxide is contacted with an alkene to obtain an alkylene oxide, whereupon the alkyl aryl hydroperoxide is converted into its corresponding alcohol. Preferably, this reaction is carried out in the presence of a catalyst. The catalyst may be homogeneous or heterogeneous. An example of a homogeneous catalyst is a catalyst comprising molybdenum. A preferred heterogeneous catalyst for such process comprises titanium on silica and/or silicate and/or silicalite. Further preferred catalysts are described, for example, in EP 345856 A1. The reaction generally proceeds at moderate temperatures and pressures, in particular at temperatures in the range of from 25 to 200° C., preferably in the range from 40 to 135° C. The precise pressure is not critical as long as it suffices to maintain the reaction mixture as a liquid or as a mixture of vapour and liquid. In general, pressures can be in the range of from 1 to 100 bar, preferably in the range from 20 to 80 bar. The alkylene oxide can be separated from the reaction product in any way known to be suitable to someone skilled in the art. For example, the liquid reaction product may be worked up by fractional distillation and/or selective extraction. The solvent, the catalyst and any unreacted alkene or hydroperoxide may be recycled for further utilization.

Preferably, the alkyl aryl compound for use in the present invention is ethylbenzene, which is converted in step (f) into 1-phenylethanol. If the alkyl aryl compound is ethylbenzene such process generally further comprises: (g) separating at least part of the 1-phenylethanol from the reaction mixture obtained in step (f), and (h) converting at the 1-phenylethanol obtained in step g) into styrene. Processes which can be used for this step have been described in WO1999042425 and WO1999042426. However, any suitable process known to someone skilled in the art can in principle be used.

Alternatively, for example when using cumene as the alkyl aryl compound for the oxidation, the alcohol obtained following the epoxidation with the hydroperoxide can be recovered from the epoxidation product and undergo dehydration/hydrogenation or hydrogenolysis to form cumene again and be recycled to step (a).

Alkyl phenyl alcohol produced in the process of the present invention may further be dehydrated or subjected to hydrogenolysis to produce the phenylalkyl which may be recycled, thus, avoiding completely the formation of the co-product.

The alkene used in the process of the present invention will depend on the alkylene oxide to be prepared. Preferably, the alkene contains from 2 to 10 carbon atoms, more preferably from 2 to 8 carbon atoms. In a preferred embodiment of the present invention, the alkene is propylene and the corresponding alkylene oxide is propylene oxide.

Processes and catalysts which can be used for the epoxidation step have been described in EP0345856, WO2005005402, WO2005016903 and WO2007128666. However, any suitable process and catalysts known to someone skilled in the art can in principle be used.

The apparatus for use in the process of the present invention, e.g. an industrial setup, comprises:

a reactor system for reacting alkyl aryl compound and oxygen to provide a liquid product stream comprising alkyl aryl hydroperoxide and alkyl aryl compound, and a vapour stream comprising alkyl aryl compound and oxygen;

a condensing column for condensing and contacting at least part of the vapour stream comprising alkyl aryl compound and oxygen with a basic aqueous solution to obtain a neutralised, condensed stream comprising alkyl aryl compound and a lean vapour stream;

a separation system comprising a coalescer for separating at least part of the neutralised, condensed stream into spent aqueous phase and a purified alkyl aryl compound stream; and a recycle conduit for recycling at least part of the purified alkyl aryl compound stream to the reactor system.

The apparatus may be arranged or configured to carry out any of the process steps hereinabove described.

Aspects of the present invention also envisage the replacement of the coalescer with another component serving the same or similar purpose. For example, removal of alkali metal to levels as hereinabove defined might also be achievable with a centrifuge.

Thus, from yet another aspect of the invention, there is provided a process for preparing an alkylene oxide comprising preparing an alkyl phenyl hydroperoxide and contacting the alkyl phenyl hydroperoxide with an alkene in an epoxidation reaction to obtain an alkylene oxide and an alkyl phenyl alcohol, wherein the alkyl phenyl hydroperoxide is prepared by a process comprising:

(a) reacting an alkyl aryl compound and oxygen to produce a reaction mixture comprising alkyl phenyl hydroperoxide, alkyl aryl compound and oxygen;

(b) separating at least a part of the reaction mixture into a product stream comprising alkyl phenyl hydroperoxide and a stream comprising alkyl aryl compound;

(c) mixing at least a part of the separated alkyl aryl compound stream with a basic aqueous solution;

(d) separating at least a part of the mixture of step (c) to obtain a separated organic phase containing alkyl aryl compound and less than 5 ppm wt. alkali metal, and a separated aqueous phase; and (e) recycling at least a part of the separated organic phase containing alkyl aryl compound to step (a).

In a preferred embodiment of the process of the present invention, alkyl phenyl alcohol and/or alkyl phenyl ketone produced during step (a) and/or the subsequent epoxidation reaction is converted to the corresponding aromatic alkene.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects, unless incompatible therewith. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied.

In this specification, references to properties are—unless stated otherwise—to properties measured under ambient conditions, i.e. at atmospheric pressure and at a temperature of about 20° C.

Figure 2:
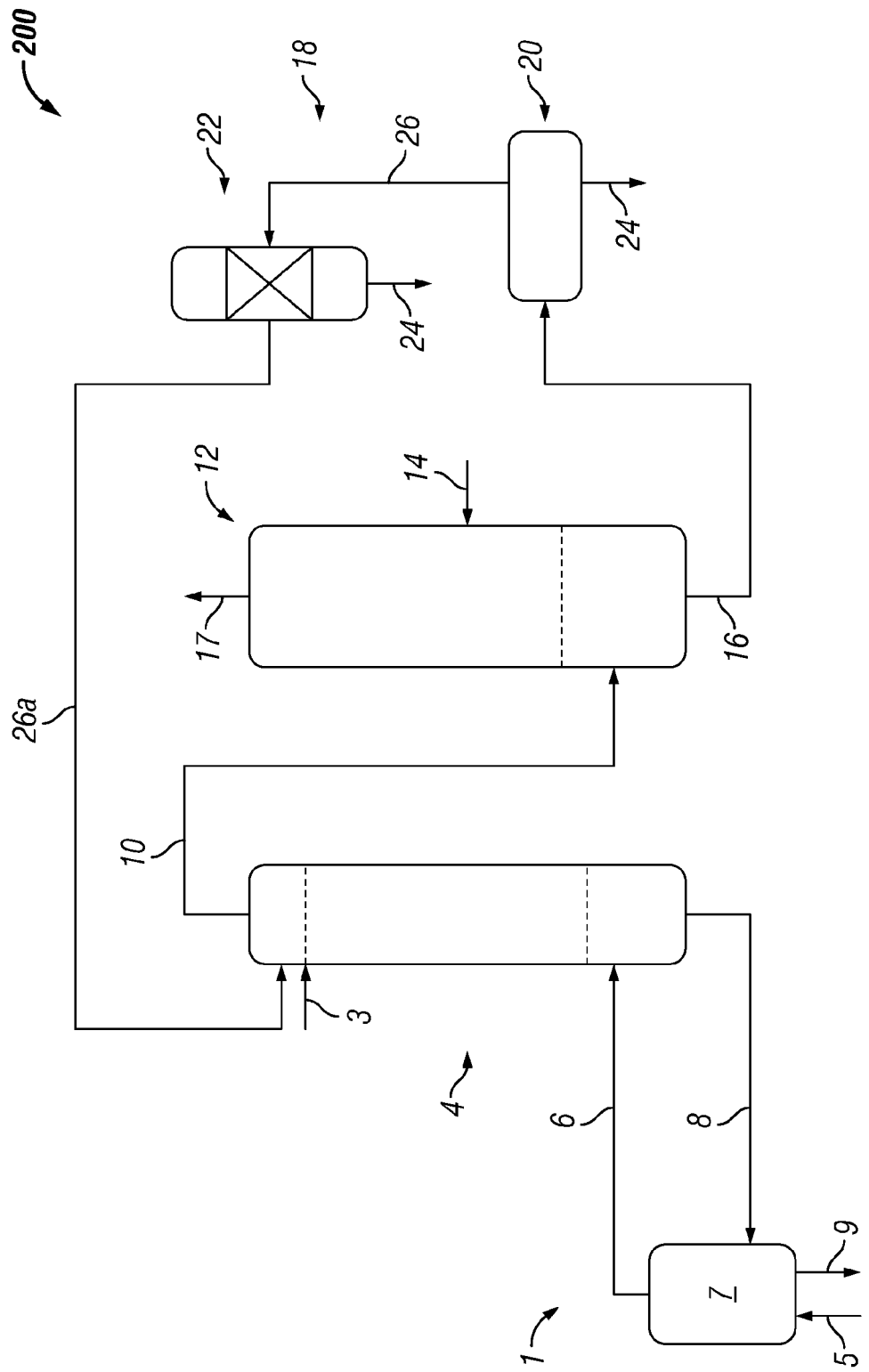
FIG. 2 depicts an embodiment of the invention.

Embodiments of the present invention will now be further described with reference to the accompanying drawings of which:

FIG. 1 is a schematic view of an industrial setup for preparing ethyl benzene hydroperoxide in which a drop in selectivity was observed;

FIG. 2 is a schematic view of an industrial setup for preparing ethyl benzene hydroperoxide in accordance with steps (a) to (e) of the process of the present invention.

A. Identification of Selectivity Drop Problem

A decline in selectivity was observed in an industrial setup for preparing ethyl benzene hydroperoxide shown schematically in FIG. 1.

The industrial setup 2 comprised a conventional reactor system 1 of four reactors in series (shown schematically as one in FIG. 1) for reacting a heated stream of ethyl benzene (EB) 8 and oxygen ($O_2$) in a stream of air 5, to provide a reaction mixture 7 comprising ethyl benzene hydroperoxide (EBHP), ethyl benzene and oxygen.

The reaction mixture 7 was separated in the reactor system 1 into a liquid product stream 9 comprising EBHP and EB, removed from the reactor for further purification to an end product, and a vapour (offgas) stream 6 comprising EB and oxygen/air.

The vapour stream 6 was fed from the reactor system to a heat recovery column 4, where it was contacted with liquid EB 3, 26 to be fed into the reactor system 1 as the heated stream of ethyl benzene 8.

From the heat recovery column 4 the remaining vapour stream 10 was passed to a condensing column 12 for contacting the vapour stream 10 with a stream of basic aqueous solution 14 to obtain a neutralised, condensed stream 16 and vent gas 17.

The neutralised condensed stream 16 was passed to a separating system 18 comprising a conventional phase-separation vessel 20. In this vessel 20 the neutralised condensed stream was separated into spent aqueous phase 24 and a purified ethyl benzene stream 26.

The purified ethyl benzene stream 26 was recycled to the heat recovery column 4 and ultimately to the reactor system via the heated liquid stream 8.

In this setup 2 a creeping downward trend in selectivity of the reaction towards ethylbenzene hydroperoxide was observed in the reactor system over a period of time.

Investigating the reasons for such a creeping selectivity drop was not straightforward. A large number of variables were at play during industrial production, particularly as drops in selectivity are often masked by automatic adjustments for considerable time.

Amongst many possible causes for selectivity drops, the impact of air flow irregularities was investigated. The impact of such irregularities is masked in industrial operation by adjustments in air control valve openings and/or compressor pressure.

To study the impact of air flow irregularities, a simulation of a reactor system comprising four reactors was created to compare the impact of "regular" and "uneven" oxygen flow to the reactors on the basis shown in Table 1. Uneven flow was simulated by varying oxygen concentrations in offgas streams emerging from different sections of the reactors.

TABLE 1

| Reactor air inputs | $O_2$ conc (vol %) - regular flow | $O_2$ conc (vol %) - uneven flow |
|---|---|---|
| Reactor 1, Section 1 | 5.34 | 4.94 |
| Reactor 1, Section 2 | 5.50 | 5.90 |
| Reactor 2, Section 1 | 5.50 | 5.10 |
| Reactor 2, Section 2 | 5.50 | 5.90 |
| Reactor 3, Section 1 | 5.50 | 5.10 |
| Reactor 3, Section 2 | 5.50 | 5.90 |
| Reactor 4, Section 1 | 5.50 | 5.10 |
| Reactor 4, Section 2 | 5.50 | 5.90 |

Under these differing oxygen flow conditions, but with all other variables constant, the simulation returned the output predictions from the reactor system as shown in Table 2.

TABLE 2

| Component | Composition obtained with regular $O_2$ flow (wt %) | Composition obtained with uneven $O_2$ flow (wt %) | % deviation for uneven |
|---|---|---|---|
| $O_2$ | 2.25882E−03 | 2.09914E−03 | |
| EB | 8.70045E+01 | 8.69951E+01 | −0.011 |
| EBHP | 1.09375E+01 | 1.09299E+01 | −0.070 |
| 1-phenylethanol | 8.84732E−01 | 8.97009E−01 | 1.388 |
| Acetophenone | 9.94455E−01 | 9.98689E−01 | 0.426 |
| $H_2O$ | 1.07782E−02 | 1.10230E−02 | 2.271 |
| Benzoic acid | 1.07805E−01 | 1.08093E−01 | 0.267 |
| $N_2$ | 2.84978E−02 | 2.85896E−02 | 0.322 |
| Methane | 3.58775E−05 | 3.78282E−05 | 5.437 |
| Acetic acid | 4.49678E−03 | 4.50112E−03 | 0.097 |
| Formic acid | 3.52790E−03 | 3.53108E−03 | 0.090 |
| Phenol | 2.13930E−02 | 2.14359E−02 | 0.201 |

It is noted from the predicted outputs that more ethylbenzene is consumed, less ethylbenzene hydroperoxide (EBHP) is formed, and 1-phenylethanol and acetophenone by-product, and other contaminants, including acids, increase when the flow of oxygen to the reactors is uneven.

The outputs thus indicate that uneven air flow leads to lower selectivity to EBHP, and consequently, will adversely affect the overall production of alkylene oxide in the subsequent epoxidation reaction. Since the possibilities for masking uneven air flow are ultimately limited, e.g. by compressor pressure and maximum control valve opening, the simulation confirms that ultimately uneven oxygen supply to the reactors leads to selectivity drops in a real life industrial setup.

Evenness of air/oxygen flows in the reactors of industrial setup of FIG. 1 was thus identified as a factor determining selectivity. Even air flow is dependent on the absence/mitigation of fouling of air inlets. Fouled inlets lead to uneven air flow and it can hence be concluded from the results that fouled inlets lead to selectivity drops. There is also a reduction in capacity by the limitation of the overall amount of oxygen that can be fed to the reactor system due to the fouling of the air inlets.

To be able to measure fouling in the coalescer, a "fouling factor" was determined for the air inlets of the four reactors in the setup of FIG. 1. The "fouling factor" was calculated from control valve opening values (daily averages) of air inlets into respective first and second section of the four oxidation reactors, corrected by the square of the relevant air flows. Where control valve opening relative to square of the air flow increases this is indicative of increased fouling.

The "fouling factor" measured over a period of more than two years in the system of FIG. 1, i.e. while a selectivity drop occurred, is shown in Table 3.

TABLE 3

| Reactor air inputs (FIG. 1) | Fouling factor (Control valve opening/airflow$^2$) |
|---|---|
| Reactor 1, Section 1 | 16.9 |
| Reactor 1, Section 2 | 56.9 |
| Reactor 2, Section 1 | 88.0 |
| Reactor 2, Section 2 | 32.2 |
| Reactor 3, Section 1 | 32.9 |
| Reactor 3, Section 2 | 19.1 |

TABLE 3-continued

| Reactor air inputs (FIG. 1) | Fouling factor (Control valve opening/airflow^2) |
|---|---|
| Reactor 4, Section 1 | 16.4 |
| Reactor 4, Section 2 | 16.7 |

Notably the differences between reactors are due to selection of different sizes of control valves for the relevant sections.

B. Solution

In an attempt to address the identified cause of the loss of selectivity, the industrial setup was modified in accordance with an embodiment of the invention, to include a coalescer in the separating system 18.

With reference to FIG. 2, an industrial setup 200 in accordance with an embodiment of the invention comprises the same components as the setup 2 of FIG. 1, with like reference numerals being used for like parts, save that a coalescer 22 is installed downstream of the separation vessel 20 to further purify the purified ethyl benzene stream 26.

The coalescer comprised a horizontal coalescer separation vessel comprising fluoropolymer fibre coalescers. The flow through the coalescer was also horizontal and it was confirmed by testing that the coalescer reduced alkali metal concentration in the further purified ethyl benzene stream 26a to less than 2 ppm wt.

As aforesaid, in an industrial setup effects on selectivity are masked by other variables, as well as shutdowns. Accordingly, a direct measurement on the impact of the coalescer on selectivity was not possible. Instead, the effectiveness of the coalescer was measured by the "fouling factor", as described above in respect of the system of FIG. 1, in the knowledge (from Table 2) that fouling is linked to selectivity.

The "fouling factor" measured over a period of more than two years in the system of FIG. 2 is shown in Table 4, with the values from FIG. 1 shown for comparison.

TABLE 4

| Reactor air inputs | Fouling factor - FIG. 2 (Control valve opening/airflow^2) | Fouling factor - FIG. 1 (Control valve opening/airflow^2) |
|---|---|---|
| Reactor 1, Section 1 | 16.6 | 16.9 |
| Reactor 1, Section 2 | 40.8 | 56.9 |
| Reactor 2, Section 1 | 47.8 | 88.0 |
| Reactor 2, Section 2 | 29.4 | 32.2 |
| Reactor 3, Section 1 | 32.4 | 32.9 |
| Reactor 3, Section 2 | 18.9 | 19.1 |
| Reactor 4, Section 1 | 16.6 | 16.4 |
| Reactor 4, Section 2 | 16.1 | 16.7 |

It is noted that, especially in the front end of the reaction train, the fouling factor decreased after installation of the coalescer (i.e. in the system 200 of FIG. 2 compared to the system 2 of FIG. 1), indicating less tendency of fouling.

When taking these results in combination with the conclusion from the simulation results of Table 2, it is clear that the coalescer 22 is effective in addressing the observed selectivity drop, by addressing at least one cause thereof.

The mechanism of action of the coalescer 22 can be surmised to be a reduction in alkali metal content in the recycled ethylbenzene stream, which in turn reduces fouling and helps to maintain selectivity to EBHP.

As hereinbefore described, increases in selectivity to EBHP and reduced formation of 1-phenylethanol, acetophenone and other by-products leads to improved production of propylene oxide from EBHP and propylene in an epoxidation reaction, leading to the preparation of more propylene oxide for every molecule of co-produced styrene and also to the lower consumption of ethylbenzene for every molecule of propylene oxide produced.

What is claimed is:

1. A process for preparing an alkylene oxide comprising preparing an alkyl phenyl hydroperoxide and contacting the alkyl phenyl hydroperoxide with an alkene in an epoxidation reaction to obtain an alkylene oxide and an alkyl phenyl alcohol, wherein the alkyl phenyl hydroperoxide is prepared by a process comprising:
    (a) reacting an alkyl aryl compound and oxygen to produce a reaction mixture comprising alkyl phenyl hydroperoxide, alkyl aryl compound and oxygen;
    (b) separating at least a part of the reaction mixture into a product stream comprising alkyl phenyl hydroperoxide and a stream comprising alkyl aryl compound;
    (c) mixing at least a part of the separated alkyl aryl compound stream with a basic aqueous solution to form a mixture;
    (d) separating at least a part of the mixture of step (c) with the help of a coalescer to obtain a separated organic phase containing alkyl aryl compound, and a separated aqueous phase; and
    (e) recycling at least a part of the separated organic phase containing alkyl aryl compound to step (a).

2. The process of claim 1, wherein step (b) comprises separating at least a part of the reaction mixture into: a liquid stream comprising alkyl phenyl hydroperoxide and alkyl aryl compound; and a vapour stream comprising alkyl aryl compound and oxygen.

3. The process of claim 2, wherein at least a part of the vapour stream comprising alkyl aryl compound and oxygen is condensed and contacted with the basic aqueous solution in step (c) to form a liquid mixture for separation and recycling in steps (d) and (e).

4. The process of claim 3, wherein condensable parts of the vapour stream comprising alkyl aryl compound are condensed by contacting said stream with basic aqueous solution in step (c).

5. The process of claim 1, wherein the mixture of step (c) is separated in step (d) such that the organic phase has an alkali metal content of less than 5 ppm wt.

6. The process of claim 1, comprising, in step (d), passing the mixture of step (c) to a phase separation vessel in order to separate an amount of aqueous phase therefrom, and subsequently passing a remaining part of the mixture to a coalescer to separate a further amount of aqueous phase therefrom.

7. The process of claim 1, wherein the mixture of step (c) is separated in step (d) by contacting the mixture with a coalescer comprising fibres selected from metal, polymeric fibres, silicon treated pleated paper, and combinations thereof.

8. The process of claim 1, wherein alkyl phenyl alcohol and/or alkyl phenyl ketone produced during step (a) and/or the subsequent epoxidation reaction is converted to the corresponding aromatic alkene.

9. The process of claim 1, wherein the alkyl aryl compound is ethylbenzene and the alkyl phenyl hydroperoxide is ethyl benzene hydroperoxide.

10. The process of claim 1, wherein the alkene is propylene and the alkylene oxide is propylene oxide.

\* \* \* \* \*